(12) United States Patent
Kleyman

(10) Patent No.: US 9,033,873 B2
(45) Date of Patent: May 19, 2015

(54) SURGICAL RETRACTOR INCLUDING ROTATABLE KNOBS

(75) Inventor: Gennady Kleyman, Brooklyn, NY (US)

(73) Assignee: Covidien LP, Mansfield, MA (US)

( * ) Notice: Subject to any disclaimer, the term of this patent is extended or adjusted under 35 U.S.C. 154(b) by 572 days.

(21) Appl. No.: 13/370,338

(22) Filed: Feb. 10, 2012

(65) Prior Publication Data
US 2012/0245427 A1    Sep. 27, 2012

Related U.S. Application Data

(60) Provisional application No. 61/466,569, filed on Mar. 23, 2011.

(51) Int. Cl.
*A61B 1/32* (2006.01)
*A61B 17/02* (2006.01)
*A61B 17/34* (2006.01)

(52) U.S. Cl.
CPC ..... *A61B 17/0293* (2013.01); *A61B 2017/0225* (2013.01); *A61B 17/3423* (2013.01)

(58) Field of Classification Search
CPC ........... A61B 17/02; A61B 2017/0025; A61B 17/0293
USPC .................................................. 600/201–248
See application file for complete search history.

(56) References Cited

U.S. PATENT DOCUMENTS

| | | | |
|---|---|---|---|
| 3,807,393 A * | 4/1974 | McDonald | 600/208 |
| 5,159,921 A | 11/1992 | Hoover | |
| 5,524,644 A | 6/1996 | Crook | |
| 5,906,577 A | 5/1999 | Beane et al. | |
| 6,077,288 A | 6/2000 | Shimomura et al. | |
| 6,254,534 B1 | 7/2001 | Butler et al. | |
| 6,382,211 B1 * | 5/2002 | Crook | 128/849 |
| 6,450,983 B1 * | 9/2002 | Rambo | 602/60 |
| 6,582,364 B2 | 6/2003 | Butler et al. | |
| 6,589,167 B1 | 7/2003 | Shimomura et al. | |
| 6,723,044 B2 | 4/2004 | Pulford et al. | |
| 6,814,078 B2 * | 11/2004 | Crook | 128/849 |

(Continued)

FOREIGN PATENT DOCUMENTS

| | | |
|---|---|---|
| EP | 1312318 | 12/2005 |
| EP | 2181657 | 5/2010 |

(Continued)

OTHER PUBLICATIONS

European Search Report (9 pages) for corresponding EP12158885—mailing date Jul. 9, 2012.

(Continued)

*Primary Examiner* — Matthew Lawson

(57) ABSTRACT

A surgical access port is provided for insertion through an incision formed in a body wall of a patient. The surgical access port generally includes a sleeve assembly having a folding assembly provided at a proximal end of the sleeve assembly. The sleeve assembly includes a flexible sleeve and a flexible distal ring provided at a distal end of the flexible sleeve. A proximal end of the sleeve assembly includes a pocket formed in the sleeve material. The folding assembly is located in the pocket and generally includes a proximal ring and one or more ring knobs rotatably mounted on the proximal ring. Locking structure, in the form of a ratchet and pawl mechanism, may be provided to secure the ring knobs in position relative to the proximal ring.

9 Claims, 7 Drawing Sheets

(56) References Cited

U.S. PATENT DOCUMENTS

| | | | |
|---|---|---|---|
| 6,846,287 | B2 | 1/2005 | Bonadio et al. |
| 6,958,037 | B2 | 10/2005 | Ewers et al. |
| 7,033,319 | B2 * | 4/2006 | Pulford et al. ............... 600/208 |
| 7,081,089 | B2 | 7/2006 | Bonadio et al. |
| 7,238,154 | B2 | 7/2007 | Ewers et al. |
| 7,377,898 | B2 | 5/2008 | Ewers et al. |
| 7,393,322 | B2 | 7/2008 | Wenchell |
| 7,445,597 | B2 | 11/2008 | Butler et al. |
| 7,537,564 | B2 | 5/2009 | Bonadio et al. |
| 7,540,839 | B2 | 6/2009 | Butler et al. |
| 7,559,893 | B2 | 7/2009 | Bonadio et al. |
| 7,650,887 | B2 | 1/2010 | Nguyen et al. |
| 7,704,207 | B2 | 4/2010 | Albrecht et al. |
| 7,727,146 | B2 | 6/2010 | Albrecht et al. |
| 7,951,076 | B2 | 5/2011 | Hart et al. |
| 7,998,068 | B2 | 8/2011 | Bonadio et al. |
| 2004/0260153 | A1 | 12/2004 | Pulford et al. |
| 2005/0020884 | A1 | 1/2005 | Hart et al. |
| 2005/0148823 | A1 | 7/2005 | Vaugh et al. |
| 2005/0192483 | A1 | 9/2005 | Bonadio et al. |
| 2005/0197537 | A1 * | 9/2005 | Bonadio et al. ............... 600/208 |
| 2005/0203346 | A1 | 9/2005 | Bonadio et al. |
| 2005/0222582 | A1 * | 10/2005 | Wenchell ............... 606/108 |
| 2005/0240082 | A1 * | 10/2005 | Bonadio et al. ............... 600/208 |
| 2006/0149306 | A1 | 7/2006 | Hart et al. |
| 2006/0161050 | A1 | 7/2006 | Butler et al. |
| 2006/0223028 | A1 * | 10/2006 | Horvath ............... 433/136 |
| 2006/0247498 | A1 | 11/2006 | Bonadio et al. |
| 2007/0088204 | A1 * | 4/2007 | Albrecht et al. ............. 600/208 |
| 2007/0093695 | A1 | 4/2007 | Bonadio et al. |
| 2007/0203398 | A1 | 8/2007 | Bonadio et al. |
| 2008/0021359 | A1 * | 1/2008 | Beckman et al. ............... 602/60 |
| 2008/0021360 | A1 | 1/2008 | Fihe et al. |
| 2008/0200767 | A1 | 8/2008 | Ewers et al. |
| 2008/0281161 | A1 | 11/2008 | Albrecht et al. |
| 2008/0300467 | A1 * | 12/2008 | Schaefer ............... 600/208 |
| 2009/0187079 | A1 | 7/2009 | Albrecht et al. |
| 2010/0191064 | A1 | 7/2010 | Nguyen et al. |

FOREIGN PATENT DOCUMENTS

| | | |
|---|---|---|
| WO | WO 01/08581 | 2/2001 |
| WO | WO 03/103548 A1 | 12/2003 |
| WO | WO 2004/075741 | 9/2004 |

OTHER PUBLICATIONS

European Search Report EP08253236 dated Feb. 10, 2009.
European Search Report EP09251613 dated Mar. 24, 2011.
European Search Report EP10250526 dated Jun. 23, 2010.
European Search Report EP10250638 dated Jul. 19, 2010.
European Search Report EP10250643 dated Jun. 23, 2010.
European Search Report EP10250881 dated Aug. 18, 2010.
European Search Report EP10250885 dated Aug. 18, 2010.
European Search Report EP10250944 dated Jul. 29, 2010.
European Search Report EP10251218 dated Jun. 15, 2011.
European Search Report EP10251317 dated Oct. 15, 2011.
European Search Report EP10251359 dated Nov. 8, 2010.
European Search Report EP10251399 dated Sep. 13, 2010.
European Search Report EP10251486 dated Oct. 19, 2010.
European Search Report EP10251693 dated Feb. 3, 2011.
European Search Report EP10251718 dated Jan. 28, 2011.
European Search Report EP10251751 dated Apr. 28, 2011.
European Search Report EP10251796 dated Jan. 31, 2011.
European Search Report EP10251955 dated Feb. 21, 2011.
European Search Report EP10251983 dated Feb. 15, 2011.
European Search Report EP10251984 dated Feb. 10, 2011.
European Search Report EP10251985 dated Feb. 15, 2011.
European Search Report EP10251986 dated Mar. 7, 2011.
European Search Report dated May 7, 2012 for EP 11 19 3738.

* cited by examiner

SURGICAL RETRACTOR INCLUDING ROTATABLE KNOBS

CROSS REFERENCE TO RELATED APPLICATION

The present application claims the benefit of and priority to U.S. Provisional Application Ser. No. 61/466,569, filed on Mar. 23, 2011, the entire contents of which are incorporated herein by reference.

BACKGROUND

1. Technical Field

The present disclosure relates to a surgical retractor including rotatable knobs for a surgical access port to be inserted through an incision formed in the body of a patient. More particularly, the present disclosure relates to a surgical access port having a flexible sleeve and rotatable knobs engageable with the flexible sleeve to rotate a proximal end of the flexible sleeve against an outer surface of the patient's body.

2. Background of Related Art

Various surgical procedures are performed in a minimally invasive manner. This includes forming a small incision through a body wall of the patient and inserting an access port through the incision to protect the wound created by the incision and provide a pathway for the insertion of surgical instruments. However, minimally invasive surgery, such as laparoscopy, has several limitations. In particular, surgery of this type requires a great deal of skill in manipulating the long narrow endoscopic instruments to a remote site under endoscopic visualization. To this end, hand-assisted laparoscopic techniques and procedures have been developed. These procedures include both laparoscopic and conventional surgical methodologies. The hand assisted technique is performed in conjunction with a hand access port which is an enlarged device positionable in, for example, the insufflated abdominal cavity, through the incision.

When choosing an access port, care must be taken to ensure that the access port has sufficient length to completely pass through the body wall of the patient. Additionally, the access port must be chosen such that it does not extend too far into the body cavity and obstruct the surgical procedure. Often times it is necessary to access a large area of the body cavity with a minimal number of access ports. In this situation, the surgeon is often limited by the angle at which the surgeon can insert surgical instruments through the access port. Further, care must be taken to prevent movement of the access port during the surgical procedure.

Therefore, it is desirable to provide a surgical access port which is adjustable to provide a low-profile relative to the outer surface of the patient's body in order to achieve a greater range of access for the surgeon's hand and/or the surgical instruments inserted through the surgical access port. Additionally, it is further desirable to provide a surgical access port which can be secured or locked into position about the tissue penetrated regardless of the thickness of the tissue encountered.

SUMMARY

There is disclosed a surgical access port having a sleeve assembly including a flexible sleeve with a distal end and a proximal end, and a folding assembly positioned at the proximal end of the sleeve for folding the sleeve down toward tissue. The folding assembly includes a proximal ring and a ring knob rotatably mounted on the proximal ring. The folding assembly is located within a pocket of sleeve material formed in the proximal end of the sleeve assembly. The pocket is formed by attaching a proximal most end of the sleeve back onto itself.

The ring knob includes a ring portion rotatably mounted on the proximal ring and a handle extending from the ring portion. A locking structure is provided to secure the ring portion relative to the proximal ring. In a specific embodiment, the locking structure is a ratchet and pawl mechanism. The ratchet and pawl mechanism includes ratchet teeth formed on an outer surface of the proximal ring and a pawl tooth, formed in the ring portion, engageable with the ratchet teeth. In a more specific embodiment, the ratchet teeth cover about one quarter of the outer surface of the proximal ring.

The sleeve assembly further includes a distal ring at the distal end of the sleeve. The distal ring is flexible so as to be insertable through an incision in a patient.

There is also disclosed a surgical access port having a sleeve assembly including a flexible sleeve having a distal end and a proximal end. A pocket is formed at the proximal end of the flexible sleeve and a folding assembly is positioned within the pocket. The folding assembly includes a proximal ring and at least two ring knobs rotatably mounted on the proximal ring. The sleeve assembly includes a flexible distal ring at the distal end of the flexible sleeve.

In an alternative embodiment, the folding assembly includes at least three ring knobs rotatably mounted on the proximal ring assembly. The ring knobs are equally spaced about the proximal ring.

In a further alternative embodiment, the folding assembly includes four ring knobs rotatably mounted on the proximal ring.

There is also disclosed a method of providing a surgical access port in the body of a patient. The method includes providing a surgical access port having a sleeve assembly including a flexible sleeve having a distal end and a proximal end. The proximal end forms a pocket of sleeve material and the distal end includes a flexible distal ring. A folding assembly is provided at the proximal end of the sleeve. The folding assembly includes a proximal ring and at least two ring knobs, positioned within the pocket formed at the proximal end of the sleeve, and rotatably mounted on the proximal ring.

The distal end of the flexible sleeve and the flexible distal ring are inserted through an incision formed in a body wall of a patient by compressing the flexible distal ring and inserting the flexible distal ring distally through the incision until it passes into a body cavity. The surgical access port is tensioned in a proximal direction to bring the flexible distal ring into engagement with an inner surface of the body wall. The pockets are grasped to engage the at least two ring knobs and the at least two ring knobs are rotated through an arc sufficient to bring the pockets into engagement with an outer surface of the body wall. In one method, the at least two ring knobs are rotated through an arc of approximately 90°. In an alternative method, the at least two ring knobs are rotated through an arc greater than 90° to capture a portion of the sleeve about the pockets. In a more specific embodiment, the at least two ring knobs are rotated through an arc of approximately 270° capturing a greater portion of the sleeve about the pockets.

DESCRIPTION OF THE DRAWINGS

Various embodiments of the presently disclosed surgical access ports are disclosed herein with reference to the drawings, wherein.

DETAILED DESCRIPTION OF EMBODIMENTS

Embodiments of the presently disclosed surgical retractors including rotatable knobs or surgical access ports will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
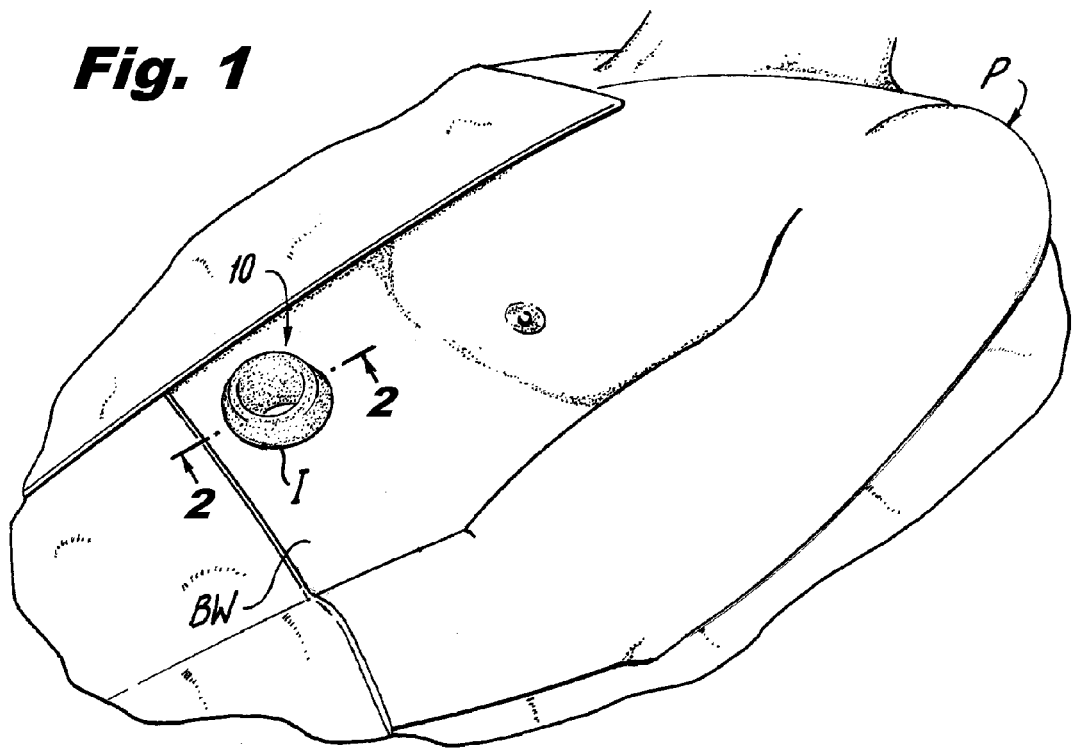
FIG. 1 is an enlarged perspective view of a surgical access port positioned through a body wall of a patient.

Referring initially to FIG. 1, there is disclosed a surgical retractor including rotatable knobs or surgical access port 10 inserted through an incision in a body wall BW of a patient P to access, for example, an abdominal cavity. Surgical access port 10 is adjustable to accommodate varying thicknesses of body tissue and provides a low-profile access port to facilitate insertion of the surgeon's hand and/or surgical instruments into a body cavity.

Figure 2:
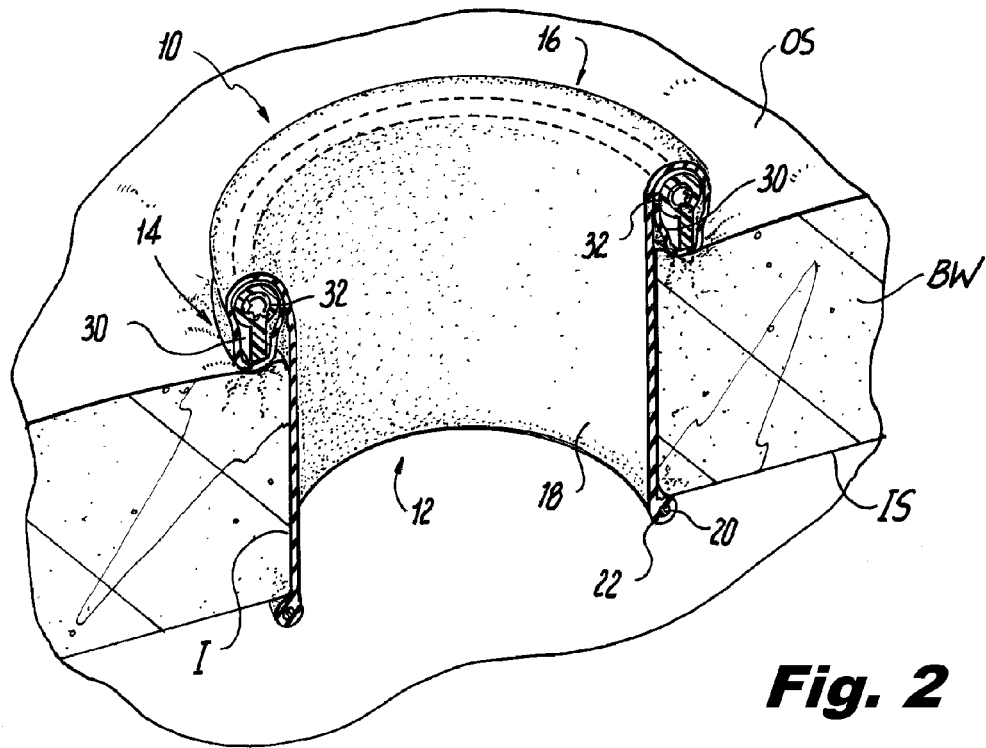
FIG. 2 is a perspective view, partially shown in section, taken along line 2-2 of FIG. 1.

Referring to FIG. 2, surgical access port 10 generally includes a sleeve assembly 12 having a sleeve wrapping or folding assembly 14 positioned within a proximal end 16 of sleeve assembly 12. Sleeve assembly 12 generally includes a flexible sleeve 18 for insertion through an incision I formed through body wall BW and a flexible distal ring 20 incorporated into a distal end 22 of flexible sleeve 18. Flexible distal ring 20 facilitates insertion of surgical access port 10 through an incision I and assists in securing surgical access port 10 against an inner surface IS of body wall BW in a manner described in more detail hereinbelow.

Figure 3:
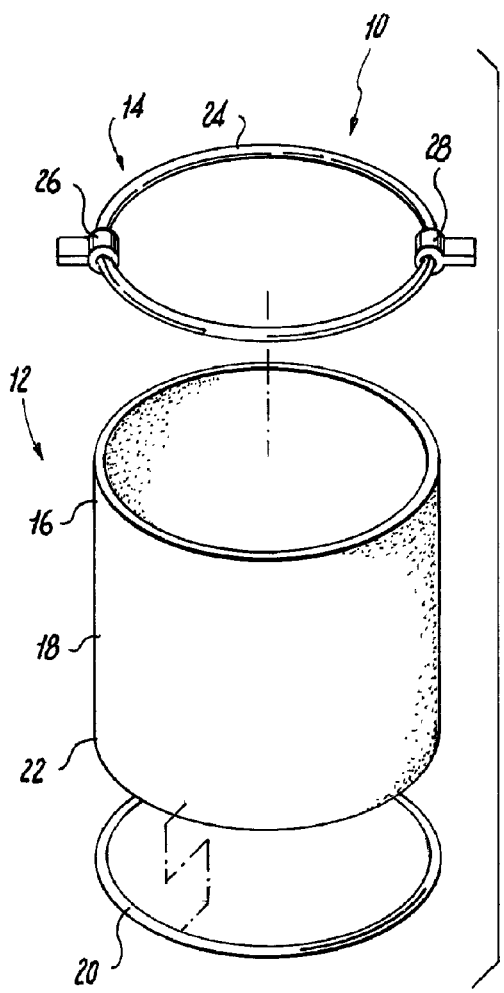
FIG. 3 is a perspective view, with parts separated, of the surgical access port of FIG. 1.

Referring now to FIG. 3, flexible sleeve 18 may be formed from a variety of materials such as, for example, sheets of plastic, woven materials, or any other flexible biocompatible materials. Similarly, flexible distal ring 20 may be formed from a variety of flexible materials such as, for example, plastics, stainless steel, shape memory alloys etc. Additionally, flexible distal ring 20 may include a split (not shown) to facilitate compressing flexible distal ring 20 during insertion into tissue. Flexible distal ring 20 is incorporated into distal end 22 of sleeve 18 by wrapping distal end 22 about flexible distal ring 20 and securing distal end 22 back onto sleeve 18 by using various methods such as, for example, gluing, welding, etc.

Folding assembly 14 generally includes a proximal ring 24 and one or more ring knobs, such as, first and second ring knobs 26 and 28 rotatably mounted on proximal ring 24. Folding assembly 14 is provided to fold proximal end 16 of sleeve assembly 12 radially outwardly and distally towards outer surface OS of body wall BW (FIG. 2) in order to secure surgical access port 10 within body wall BW.

Referring for the moment to FIG. 2, folding assembly 14 is incorporated into proximal end 16 of sleeve assembly 12 by capturing folding assembly 14 in a circumferential pocket 30 formed in proximal end 16 of sleeve assembly 12. Specifically, a proximal most end 32 of sleeve assembly 12 is inserted through proximal ring 24 and distal most end 32 is wrapped radially outwardly and back onto sleeve 18 to form circumferential pocket 30 (see also FIG. 8). Distal most end 32 is secured to flexible sleeve 18 by using various known methods such as, for example, welding, gluing etc.

Figure 4:
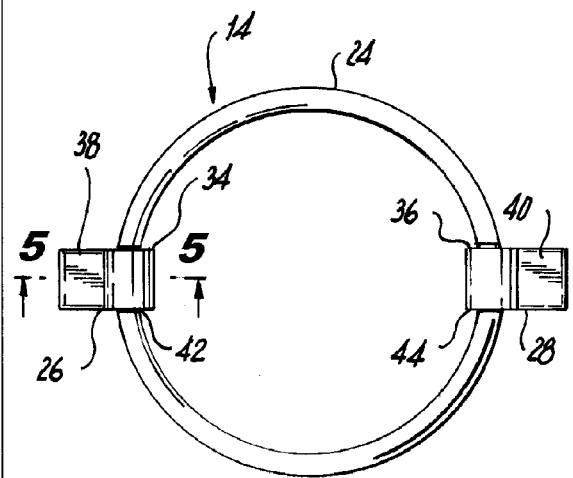
FIG. 4 is a top plan view of a wrapping or folding assembly of the surgical access port of FIG. 1.

Referring now to FIG. 4, first and second ring knobs 26 and 28, respectively, include first and second ring portions 34 and 36 having first and second handles 38 and 40 extending from first and second ring portions 34 and 36, respectively. First and second ring knobs 26 and 28 are provided to rotate and fold flexible sleeve 18 towards tissue. In order to rotate first and second ring knobs 26 and 28 about proximal ring 24, first and second ring portions 34 and 36 include respective through bores 42 and 44 positioned over proximal ring 24.

Figure 5:
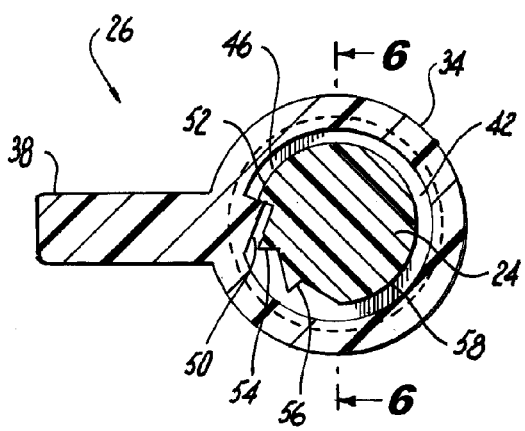
FIG. 5 is a cross-sectional view taken along line 5-5 of FIG. 4.
Figure 6:
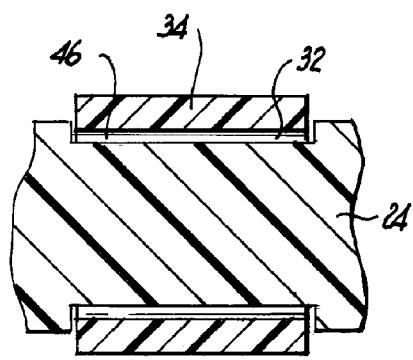
FIG. 6 is a cross-sectional view taken along line 6-6 of FIG. 5.

Referring now to FIGS. 5 and 6, while the following discussion is given with respect to first ring knob 26 it is understood that second ring knob 28 is formed and functions identically. As shown, in this embodiment, ring knob 26, and in particular ring portion 34, is positioned over a reduced area portion 46 formed in proximal ring 24. In order to secure first ring knob 26 in a final or locked position relative to proximal ring 24, first ring knob 26 and proximal ring 24 are provided with a locking or ratchet and pawl mechanism 48. Ratchet and pawl mechanism 48 includes a pawl 50 formed in through bore 42 of first ring portion 34 and one or more ratchet teeth such as, for example, ratchet teeth 52, 54 and 56 formed on an outer surface 58 of proximal ring 24.

As shown, in this embodiment, ratchet and pawl mechanism 48 is provided on only about a quarter portion of outer surface 58. This provides a 90° range of locking rotation of first ring knob 26 relative to proximal ring 24 to secure surgical access port 10 to tissue in a manner described in more detail hereinbelow. In an alternative embodiment, ratchet teeth may be provided about oral or part of outer surface 58 of proximal ring 24.

Figure 7:
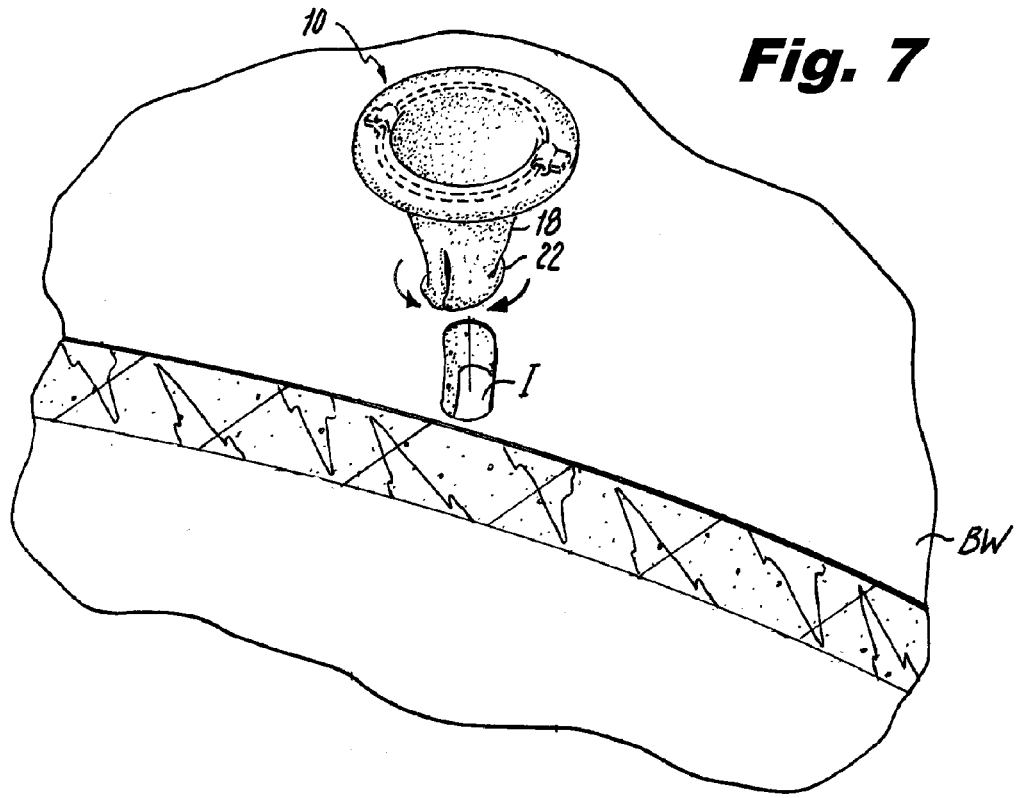
FIG. 7 is a perspective view, partially shown in section, illustrating initial insertion of the surgical access port into an incision formed through the body wall of the patient.
Figure 8:
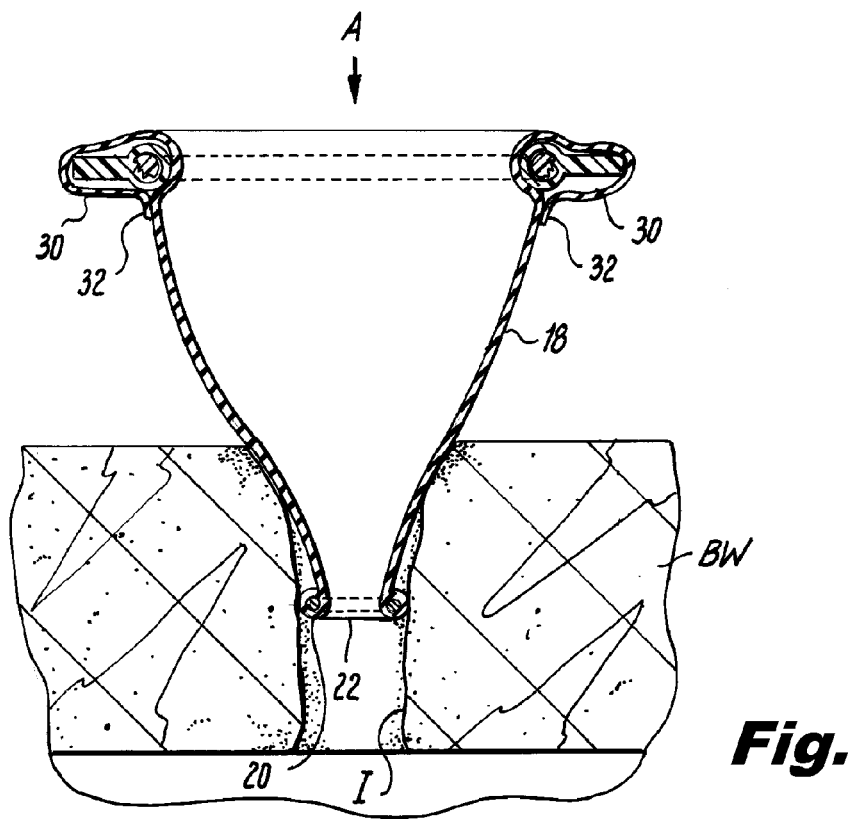
FIG. 8 is a cross-sectional view illustrating the insertion of a distal end of the surgical access port into the incision formed through the body wall of the patient.

Referring now to FIGS. 7-11, and initially with regard to FIGS. 7 and 8, the use of surgical access port 10 will now be described. Initially, an incision I is formed through body wall BW, for example, the abdominal wall, of patient P (FIG. 1). Surgical access port 10 is positioned adjacent incision I and distal end 22 of sleeve 12, including flexible distal ring 20, is compressed so as to fit through incision I.

Figure 9:
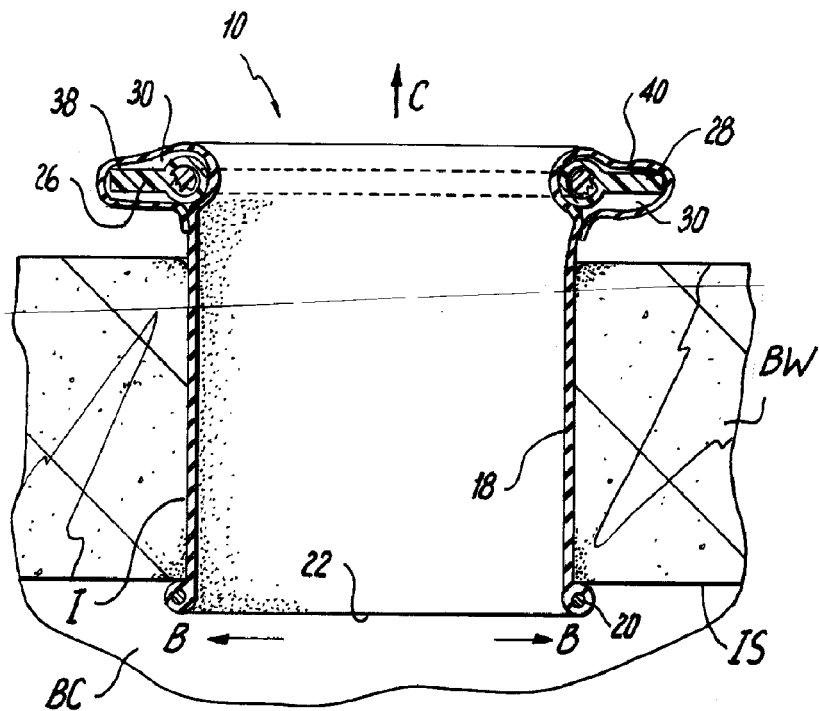
FIG. 9 is a cross-sectional view illustrating the complete insertion of the surgical access port into the incision.

Referring now to FIGS. 8 and 9, surgical access port 10 continues to be advanced through incision I in the direction of arrow A (FIG. 8) until distal end 22 of sleeve 18 and flexible distal ring 20 pass into a body cavity BC of patient P. Once flexible distal ring 20 enters body cavity BC, flexible distal ring 20 expands to its original diameter or condition opening distal end 22 of sleeve 18 to body cavity BC. Thereafter, surgical access port 10 is drawn proximally in the direction of arrow C tensioning distal end 22 of sleeve 18 and flexible distal ring 20 against an inner surface IS of body wall BW (FIG. 9).

Figure 10:
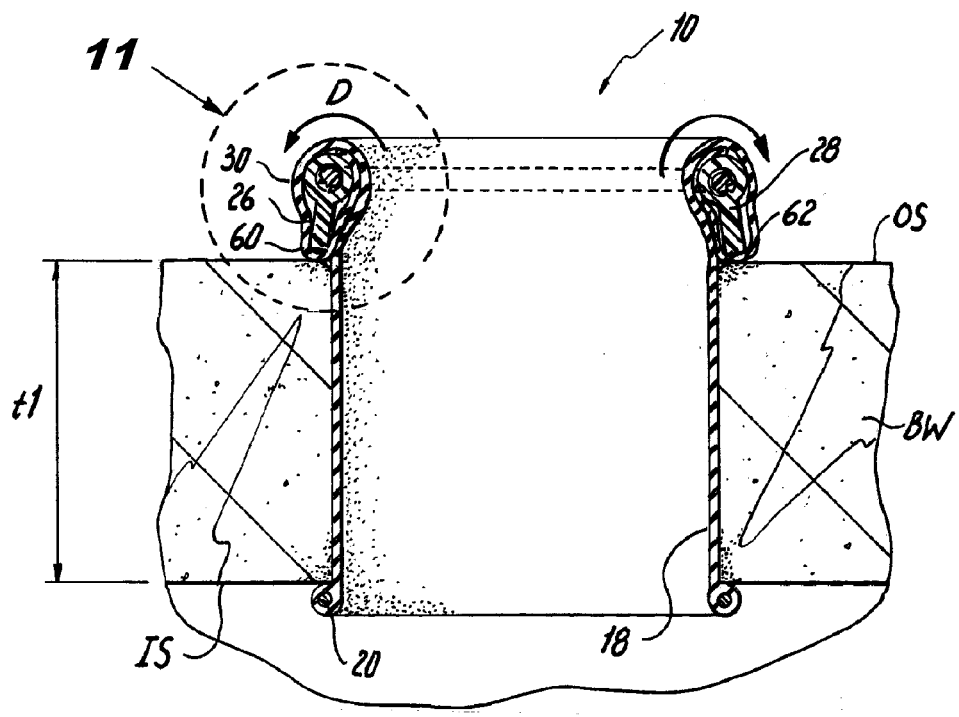
FIG. 10 is a cross-sectional view illustrating the actuation of the folding assembly to bring a proximal end of the surgical access port into contact with an outer surface of the body wall.

Referring to FIGS. 9 and 10, first and second handles 38 and 40 of first and second ring knobs 26 and 28 are grasped by pinching pocket 30 and are rotated downwardly through an approximately 90° arc until outer ends 60 and 62 of first and second handles 38 and 40, respectively, are brought adjacent outer surface OS of body wall BW (FIG. 10).

Figure 11:
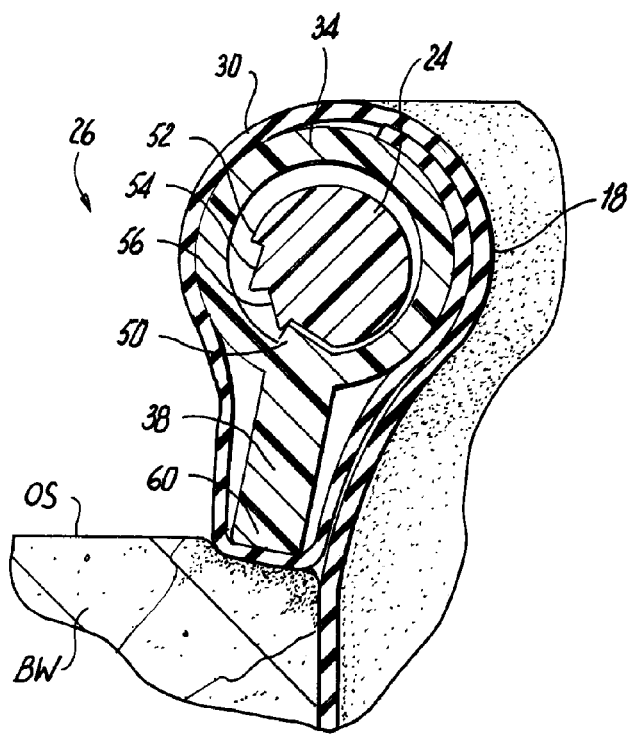
FIG. 11 is an enlarged area of detail view of FIG. 10.

As best shown in FIG. 11, as outer end 60 of first handle 38 is rotated through the 90° arc, pawl 50 in first ring portion 34 of first ring knob 26 engages ratchet teeth 52, 54 and 56 on proximal ring 24 to thereby incrementally secure first handle 38 as it is rotated. While pawl 50 in first ring portion 34 of first ring knob 26 is illustrated as engaged with ratchet 56 on proximal ring 24, pawl 50 may be engaged with either of the preceding ratchet teeth 52 and 54 depending upon the thickness of the tissue, for example, thickness t1 of body wall BW, encountered. It should be noted that, as pocket 30 of sleeve assembly 12 moves distally, proximal ring 24 also moves distally but does not rotate with the rotation of first ring knob 26. Further, it will be appreciated that second ring knob 28 is operated simultaneously with first ring knob 26 and functions in identical manner.

In this manner, proximal end 16 of sleeve assembly 12 is secured against outer surface OS of body wall BW while distal end 22 of sleeve 18 is secured against inner surface IS of body wall BW to thereby firmly secure surgical access port 10 through incision I in body wall BW. As best shown in FIG. 2, in the fully secured condition, surgical access port 10 provides a low profile and incrementally adjustable access port to facilitate insertion of surgical instruments therethrough.

Figure 12:
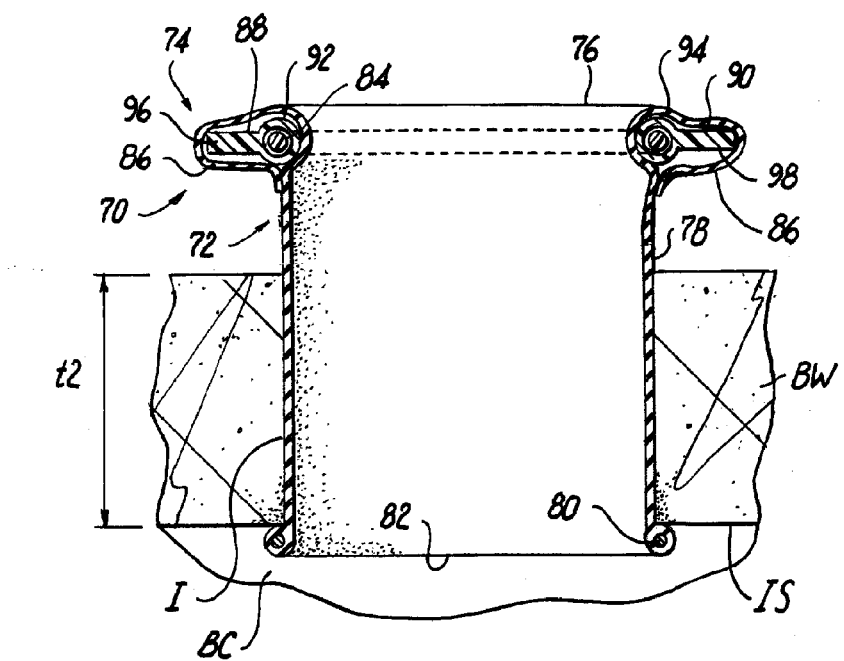
FIG. 12 is a cross-sectional view of an alternative embodiment of a surgical access port inserted through an incision in the body wall of a patient.

Referring now to FIGS. 12-15, and initially with regard to FIG. 12, there is disclosed an alternative embodiment of a surgical access port 70 for insertion through an incision I of a body wall BW having a tissue thickness t2 less than tissue thickness t1 described herein above. Surgical access port 70 is substantially identical to surgical access port 10 described herein above and generally includes a sleeve assembly 72 having a wrapping or folding assembly 74 positioned within a proximal end 76 of sleeve assembly 72. Sleeve assembly 72 includes a flexible sleeve 78 having a flexible distal ring 80 provided within a distal end 82 of flexible sleeve 78.

Folding assembly 74 generally includes a proximal ring 84 positioned within a circumferential pocket 86 of sleeve 78 and first and second ring knobs 88 and 90 are rotatably mounted on proximal ring 84 in a manner described herein above with respect to proximal ring 24 and first and second ring knobs 26 and 28. First and second ring knobs 88 and 90 include respective first and second ring portions 92 and 94, surrounding proximal ring 84, and respective first and second handles 96 and 98.

Figure 13:
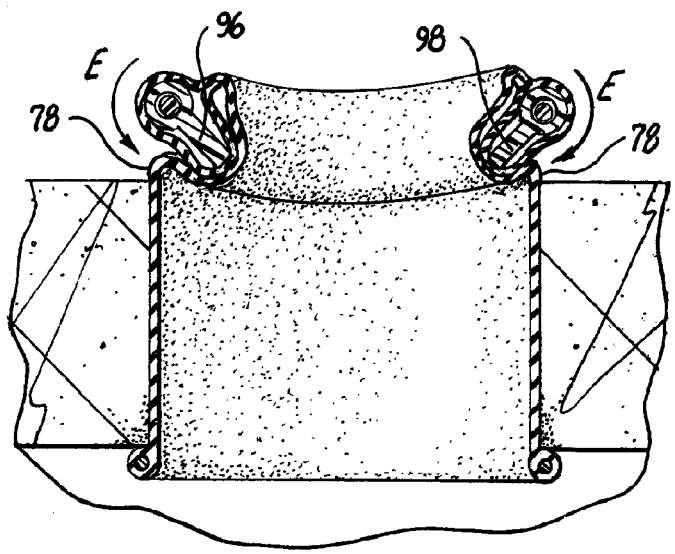
FIG. 13 is a cross-sectional view of the surgical access port of FIG. 12 during an initial actuation of the folding assembly.
Figure 14:
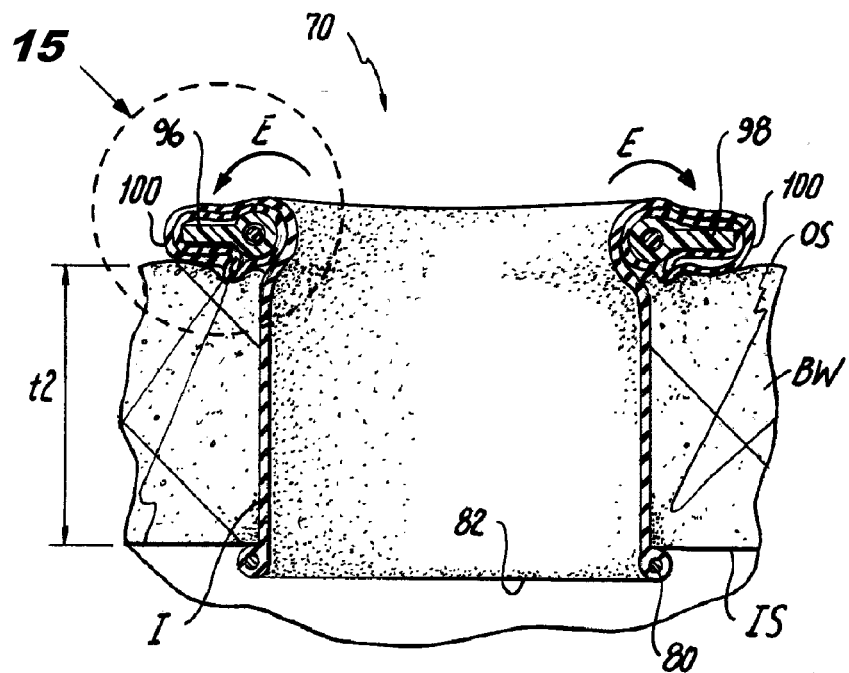
FIG. 14 is a cross-sectional view of the surgical access port of FIG. 12 with a proximal end of the surgical access port brought into engagement with an outer surface of the body wall.

Referring to FIGS. 12-14, the use of surgical access port 70 will now be described. Initially, with regard to FIGS. 12 and 13, surgical access port 78 is inserted through an incision I until flexible distal ring 80 and distal end 82 of sleeve 78 enter body cavity BC. Surgical access port 70 is tensioned to bring distal end 82 of sleeve 78 securely into engagement with an inner surface IS of body wall BW. Thereafter, first and second handles 96 and 98 are grasped by pinching pockets 86 and are rotated in direction of arrows E (FIG. 13) through an arc greater than 90°. This causes handles 96 and 98 to engage and begin to rotate sleeve 78 radially inwardly.

Referring now to FIG. 14, first and second handles 96 and 98 continued to be rotated through an arc greater than 270° thereby causing a captured portion 100 of sleeve 78 to be pressed down against an outer surface OS of body wall BW. First and second handles 96 and 98 are rotated through an arc greater than 270°, from the initial position illustrated in FIG. 12, to prevent first and second handles 96 and 98, along with captured portion 100 of sleeve 78, from impinging into sleeve 78 and thereby obstructing any surgical instruments inserted therethrough. In this manner, surgical access port 70 is secured through incision I in body wall BW.

Figure 15:
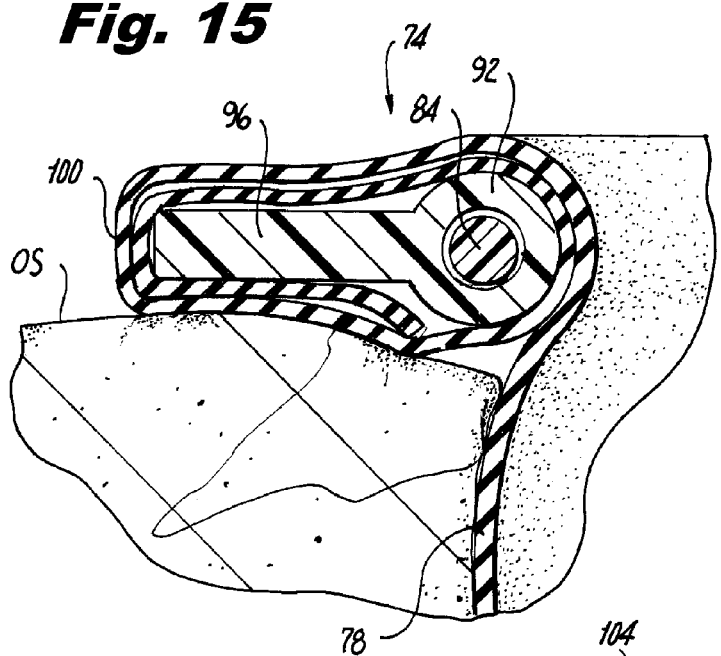
FIG. 15 is an enlarged area of detail view of FIG. 14.

With specific reference to FIG. 15, it can be seen that, unlike folding assembly 14 described herein above, folding assembly 74 of surgical access port 70 does not include a ratchet and pawl mechanism. This is due to the unknown number of rotations of first and second ring knobs 88 and 90 and captured portion 100 of sleeve 78. However, alternatively, a ratchet and pawl may can is a may be included over a portion or all of an outer surface 102 of proximal ring 84 to incrementally lock first ring knob 88 relative to proximal ring 84 depending upon the thickness of tissue t2 encountered (FIG. 14).

Figure 16:
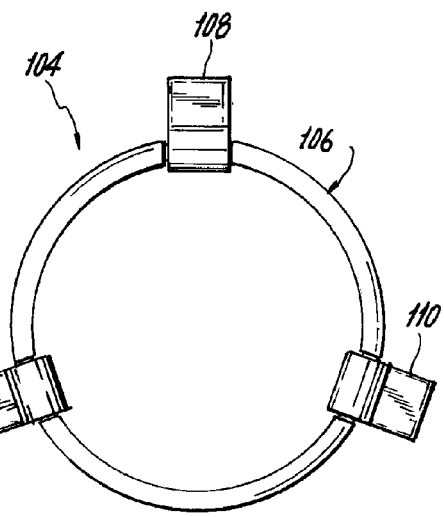
FIG. 16 is an alternative embodiment of the presently disclosed folding assembly.

Referring now to FIG. 16, there is disclosed an alternative folding assembly 104, having three proximal ring knobs, including a proximal ring 106 and first, second and third ring knobs 108, 110 and 112. First second, and third ring knobs 108, 110 and 112, along with proximal ring 106, may be formed with or without an inter-engaging ratchet and pawl mechanism.

Figure 17:
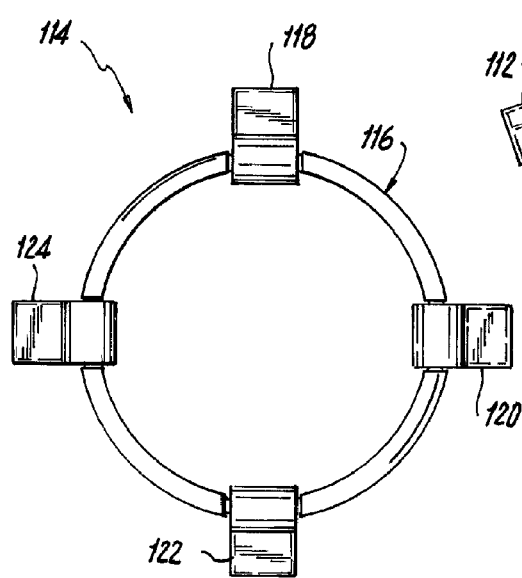
FIG. 17 is a further alternative embodiment of the presently disclosed folding assembly.

Similarly, with reference to FIG. 17, there is disclosed an alternative folding assembly 114 having a proximal ring 116 and four ring knobs 118, 120, 122 and 124. Likewise, ring knobs 118, 120, 122 and 124, along with proximal ring 116, may be formed with or without a ratchet and pawl mechanism.

It will be understood that various modifications may be made to the embodiments disclosed herein. For example, one or more ring knobs may be provided to wrap or fold the proximal end of the sleeve against tissue. Alternatively, some of the ring knobs of the folding assembly may include locking structure while the remaining ring knobs do not. Further, alternative locking structure may be provided between the ring knobs and the proximal ring, such as, for example, ball detent mechanisms, progressive adhesive structures, etc. Additionally, the disclosed proximal and distal rings may have shapes other than circular, such as, for example, rectangular, polygonal, etc. Although the access port of the present disclosure has been described to access an abdominal cavity through an incision in the abdominal wall, the access device of the present disclosure may be modified for use in other procedures, such as, for example, thoracic procedure. Therefore, the above description should not be construed as limiting, but merely as exemplifications of particular embodiments. Those skilled in the art will envision other modifications within the scope and spirit of the claims appended hereto.

The invention claimed is:
1. A surgical access port for use in a tissue tract, the surgical access port comprising:
a flexible sleeve having a distal ring at a distal end and a proximal ring at a proximal end; and a plurality of ring knobs rotatably mounted on the proximal ring and configured to roll the flexible sleeve around the proximal ring so as to shorten the flexible sleeve and thereby retract the tissue tract, each ring knob of the plurality of ring knobs including a ring portion rotatably mounted about the proximal ring and a handle portion extending radially outward from the ring portion, wherein the plurality of ring knobs are located within a pocket of sleeve material formed in the proximal end of the flexible sleeve.

2. The surgical access port as recited in claim 1, wherein the pocket is formed by attaching a proximal-most end of the flexible sleeve back onto itself.

3. The surgical access port as recited in claim 1, further including a ratchet and pawl mechanism configured to secure the ring portion relative to the proximal ring.

4. The surgical access port as recited in claim 3, wherein the ratchet and pawl mechanism includes ratchet teeth formed on an outer surface of the proximal ring and a pawl tooth formed in the ring portion, the pawl tooth being engageable with the ratchet teeth.

5. The surgical access port as recited in claim 4, wherein the ratchet teeth cover one quarter of the outer surface of the proximal ring.

6. The surgical access port as recited in claim 1, wherein the distal ring is flexible.

7. The surgical access port as recited in claim 1, wherein the plurality of ring knobs include at least three ring knobs rotatably mounted on the proximal ring.

8. The surgical access port as recited in claim 7, wherein the at least three ring knobs are equally spaced about the proximal ring.

9. The surgical access port as recited in claim 1, wherein the plurality of ring knobs include four ring knobs rotatably mounted on the proximal ring.

\* \* \* \* \*